US00PP25597P2

(12) United States Plant Patent
Turner

(10) Patent No.: US PP25,597 P2
(45) Date of Patent: May 26, 2015

(54) ***PHORMIUM* PLANT NAMED 'TRIDENT'**

(50) Latin Name: ***Phormium cookianum*×*Phormium tenax***
Varietal Denomination: Trident

(71) Applicant: Paul Turner, Auckland (NZ)

(72) Inventor: Paul Turner, Auckland (NZ)

( * ) Notice: Subject to any disclaimer, the term of this patent is extended or adjusted under 35 U.S.C. 154(b) by 155 days.

(21) Appl. No.: 13/986,797

(22) Filed: Jun. 5, 2013

Related U.S. Application Data

(60) Provisional application No. 61/689,513, filed on Jun. 7, 2012.

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Penny J. Aguirre

(57) ABSTRACT

A new cultivar of hybrid *Phormium* named 'Trident' that is characterized by its foliage with upper leaf surfaces that are variegated with centers that are green-bronze with thin stripes of red through the center area and broad margins that are red-deep pink with a very thin strip of deeper red on the leaf edge, its young foliage that is distinctly red in appearance, its upright plant habit, and its large plant height relative to other cultivars of *Phormium*.

2 Drawing Sheets

Botanical classification: *Phormium cookianum*×*Phormium tenax*.

Cultivar designation: 'Trident'.

BACKGROUND OF THE INVENTION

The present invention relates to a new and distinct cultivar of *Phormium* named 'Trident', an interspecific hybrid of *Phormium cookianum*×*Phormium tenax* and referred to hereafter by its cultivar name, 'Trident'. The new cultivar is grown for use as a foliage plant for landscape and container use.

The Inventor discovered the new cultivar summer of 2005 as a naturally occurring chimeral mutation of *Phormium* 'Rainbow Queen' (not patented) in a container block in his nursery in Auckland, New Zealand.

Asexual propagation of the new cultivar was first accomplished by division in autumn of 2005 in Auckland, New Zealand by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Trident' as a new and unique cultivar of *Phormium*.

1. 'Trident' exhibits foliage with upper leaf surfaces that are variegated with centers that are green-bronze with thin stripes of red through the center area and broad margins that are red-deep pink with a very thin strip of deeper red on the leaf edge.
2. 'Trident' exhibits foliage with the lower leaf surface being primarily red in color.
3. 'Trident' exhibits young foliage that is distinctly red in appearance.

4. 'Trident' exhibits an upright plant habit.
5. 'Trident' exhibits a large plant height relative to other cultivars of *Phormium*; reaching 70 to 120 cm in height.

'Trident' can be compared to the parent plant, 'Rainbow Queen'. 'Rainbow Queen' differs from 'Trident' in having foliage with paler green-bronze centers, thinner and paler red-pink margins, coloration that is retained less on older leaves and lower leaf surfaces that are less red in color. 'Rainbow Queen' also differs in having a shorter plant height. 'Trident' can also be compared to the cultivars 'Rainbow Chief' (not patented) and 'Jubilee' (U.S. Plant Pat. No. 19,059). Both are similar to 'Trident' in having leaves with red and green-bronze variegation. 'Rainbow Chief' differs in having foliage with paler coloration, thinner red margins, and lower leaf surfaces that are bronze-green rather than red. 'Jubilee' differs from 'Trident' in having a more open and arching plant habit and having a shorter plant height.

BRIEF DESCRIPTION OF THE DRAWING

The accompanying colored photographs illustrate the overall appearance and distinct characteristics of the new *Phormium*. The photographs were taken of a two year-old plant of 'Trident' as grown outdoors in a one-gallon container in Auckland, New Zealand.

Figure 1:
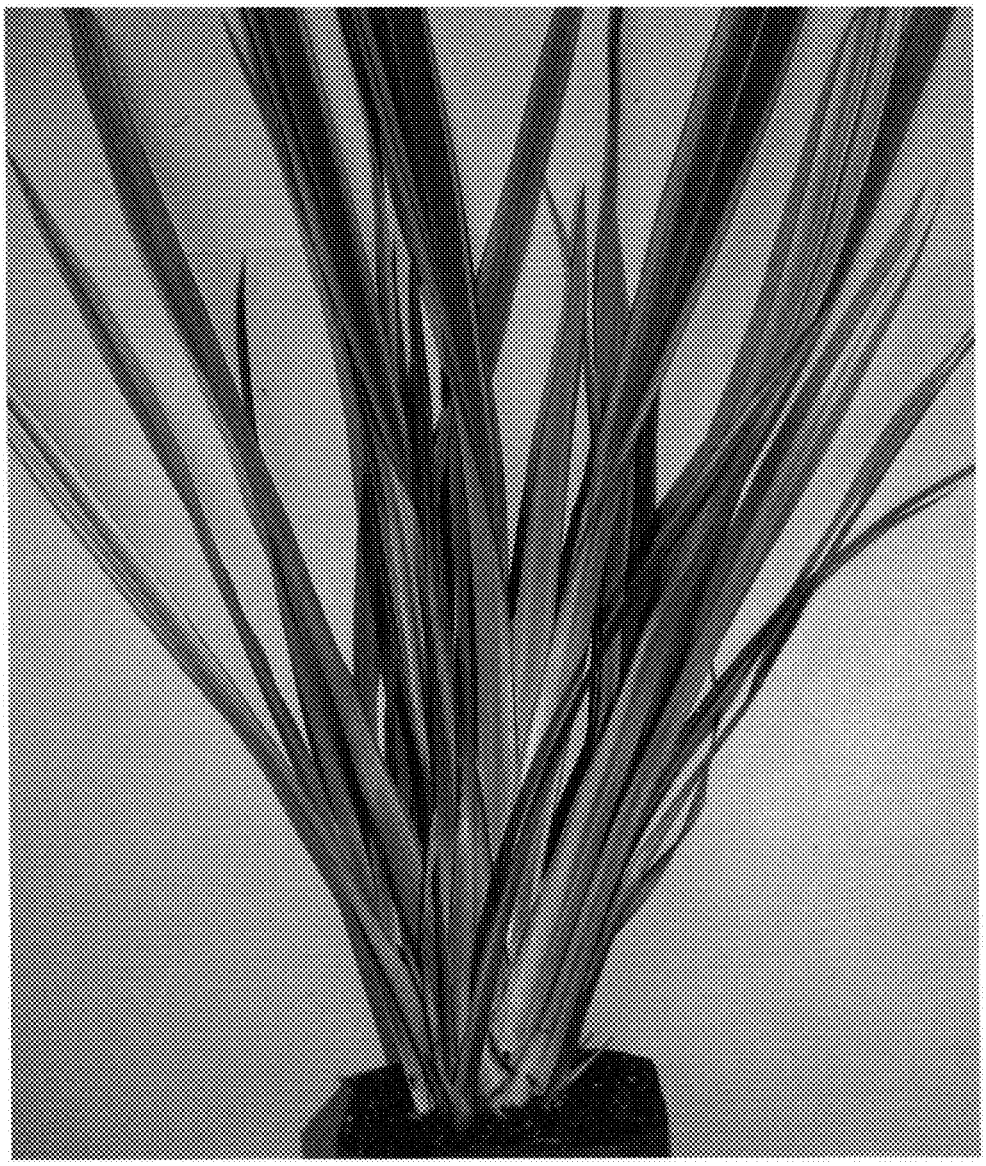
FIG. 1 provides a side view of 'Trident'.
Figure 2:
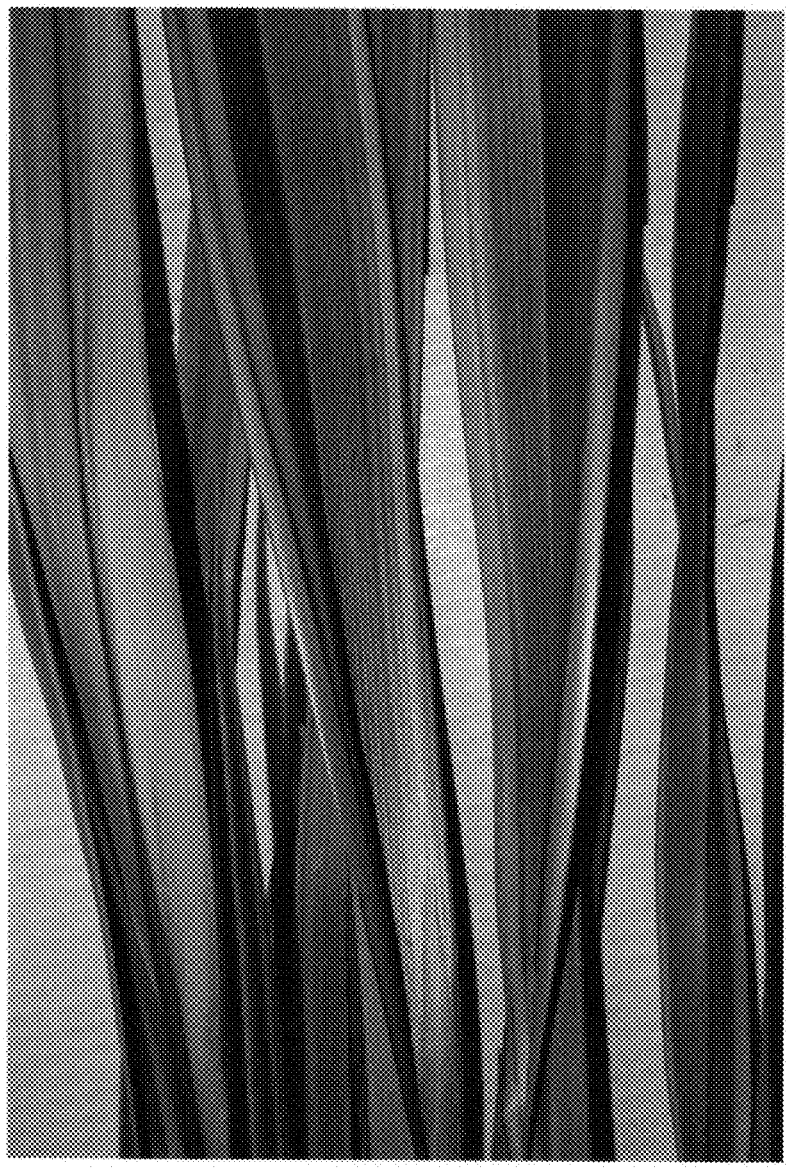
FIG. 2 provides a close-up view of the mature foliage of 'Trident'.

The colors in the photographs may differ slightly from the color values cited in the detailed botanical description, which accurately describe the colors of the new *Phormium*.

DETAILED BOTANICAL DESCRIPTION OF THE PLANT

The following is a detailed description of two year-old plants of the new cultivar as grown outdoors in one-gallon containers in Auckland, New Zealand. The plants were grown under average day temperatures of 20° to 27° C. and average night temperatures of 12° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—No flower production has been observed.

*Plant type*.—Perennial, evergreen.

*Plant habit*.—Clump-forming and upright.

*Height and spread*.—Reaches 70 to 120 cm in height and 40 to 50 cm in width when in grown in a one-gallon container.

*Hardiness*.—U.S.D.A. Zones 9a to 10b, tolerant to high temperatures of 40° C. and low temperatures of −5° C.

*Diseases and pests*.—No unique susceptibility or resistance to diseases or pests has been observed.

*Root description*.—Fibrous with some larger fleshy roots, 2 to 4 mm in diameter, vigorous, 14C in color.

*Propagation*.—Division.

*Growth rate*.—Vigorous for *Phormium* with a moderate rate of new fan development (typical of *P. tenax*), produces about 4 new fans from a single fan in 12 months of growth.

*Root development*.—Divisions take 6 to 8 weeks to develop new roots when grown at 20° C.

*Stem description*.—Stem-less, leaves are equitant from base.

Foliage description:

*Leaf shape*.—Lanceolate/Lorate.

*Leaf division*.—Simple.

*Leaf base*.—Sheathed, overlapping.

*Leaf apex*.—Acuminate.

*Leaf venation*.—Parallel, not prominent, same color as leaves, mid rib protruding on lower surface.

*Leaf margins*.—Entire.

*Leaf attachment*.—Sheathed, lacks petioles.

*Leaf arrangement*.—Equitant.

*Leaf number*.—Average of 12 as grown in a one-gallon container.

*Leaf orientation*.—Held upright and becomes slightly arching, moderately concave with medium to sharp keel.

*Leaf substance*.—Stiff, leathery, durable.

*Leaf surface*.—Smooth with fine longitudinal lines, upper surface satiny, lower surface slightly glaucous.

*Leaf color*.—Young leaves upper surface; centers N186C and 200B, outer edge of leaves 58A and 184C with very thin margins 183A, young leaves under surface; centers dull N186C and 200B with occasional stripes 184A, outer edge of leaves dulled 184B with margins 183A, mature leaves upper surface; centers N186C and N200A, outer edges of leaves 58A and184B with very thin margins 183A, mature leaves lower surface; centers N186C and 200B occasional stripes of 58B and 184C, outer edge of leaves 184B and 58A with a very thin margin 183A.

*Leaf size*.—60 to 120 cm in length and 4 to 5 cm in width.

It is claimed:

1. A new and distinct cultivar of *Phormium* plant named 'Trident' as herein illustrated and described.

* * * * *